United States Patent
Fukao et al.

(10) Patent No.: US 6,344,557 B1
(45) Date of Patent: Feb. 5, 2002

(54) PROCESS FOR PRODUCING ε-CAPROLACTAM

(75) Inventors: Masami Fukao, Shiga; Kan Takamine, Osaka; Tomokazu Nakamura, Toyonaka, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/674,164

(22) PCT Filed: Apr. 21, 1999

(86) PCT No.: PCT/JP99/02115
§ 371 Date: Oct. 27, 2000
§ 102(e) Date: Oct. 27, 2000

(87) PCT Pub. No.: WO99/55671
PCT Pub. Date: Nov. 4, 1999

(30) Foreign Application Priority Data

Apr. 28, 1998 (JP) ............................................. 10-119602

(51) Int. Cl.$^7$ ............................................. C07D 201/16
(52) U.S. Cl. ....................................................... 540/540
(58) Field of Search .......................................... 540/540

(56) References Cited

U.S. PATENT DOCUMENTS 4,968,793 A * 11/1990 Kitamura et al. ............ 540/536
5,304,643 A * 4/1994 Kajikuri et al. ............. 540/336
5,502,184 A * 3/1996 Kajikuri et al. ............. 540/536

FOREIGN PATENT DOCUMENTS

| JP | A4187672 | * | 7/1992 |
| JP | A7109255 | * | 4/1995 |
| JP | A7118228 | * | 5/1995 |
| JP | A7179419 | * | 7/1995 |
| JP | A7196606 | * | 8/1995 |

OTHER PUBLICATIONS

Benson et al., Organic Syntheses, O–Methylcaprolactum, pp. 588–590.*
Benson et al., Chemical Reactions of Caprolactum, vol/70, pp. 2115–2118 (1948).*

* cited by examiner

*Primary Examiner*—Bruck Kifle
(74) *Attorney, Agent, or Firm*—Birch, Stewart, Kolasch & Birch, LLP

(57) ABSTRACT

The present invention provides a method for producing ε-caprolactam which comprises the step of treating, with water, a reaction product containing 1-aza-2-alkoxy-1-cycloheptene, which is obtained by gas phase Beckmann rearrangement reaction of cyclohexanone oxime using a solid catalyst in the presence of alcohol, to eliminate the 1-aza-2-alkoxy-1-cycloheptene. The resulting ε-caprolactam usually has a 1-aza-2-alkoxy-1-cycloheptene content of 100 ppm or less, preferably 25 ppm or less, more preferably 10 ppm or less and, therefore, has low free basicity and good qualities.

12 Claims, No Drawings

PROCESS FOR PRODUCING ε-CAPROLACTAM

This application is the national phase under 35 U.S.C. §371 of PCT International Application No. PCT/JP99/02115 which has an International filing date of Apr. 21, 1999, which designated the United States of America.

FIELD OF THE INVENTION

The present invention relates to a method for producing ε-caprolactam having low free basicity. Specifically, the present invention relates to a method for producing ε-caprolactam having low free basicity which comprises a step of producing ε-caprolactam by a gas phase Beckmann rearrangement reaction of cyclohexanone oxime using a solid catalyst in the presence of alcohol.

BACKGROUND OF THE INVENTION

ε-caprolactam is an important compound as an intermediate in producing nylon-6. A method for producing ε-caprolactam from cyclohexanone oxime by gas phase Beckmann rearrangement reaction using a solid catalyst is known, and as the solid catalyst, it is known to use a boron-based catalyst, silica-alumina catalyst, solid phosphoric acid catalyst, complex metal oxide catalyst, zeolite-based catalyst and the like. Further, Japanese Patent Application Laid-Open (JP-A) Nos. 62-123167 and 63-54358 show examples using a high-silica type metallosilicate catalyst, and the selectivity in gas phase Beckmann rearrangement reaction of cyclohexanone oxime using such a catalyst system has been fairly improved as compared with conventional catalyst systems. JP-A No. 2-275850 discloses that the selectivity is further improved in a method for producing ε-caprolactam in which a lower alcohol is allowed to exist together with a solid catalyst. Moreover, JP-A 5-201965 discloses that the selectivity and catalyst life are improved when ε-caprolactam is produced by gas phase catalytic reaction of cyclohexanone oxime in allowing water to exist in the reaction system using a zeolite catalyst in the presence of alcohol and/or ether compound.

On the other hand, it is known that by allowing an alkylating agent such as dimethyl sulfate and diazomethane to act on ε-caprolactam, a corresponding 1-aza-2-alkoxy-1-cycloheptene (hereinafter, sometimes abbreviated as AAH) is synthesized. However, it is not known at all that AAH is generated as a by-product in gas phase Beckmann rearrangement reaction of an oxime in the presence of alcohol, and that one of standards for the product, free basicity, may sometimes not be satisfied when AAH remains in the product, ε-caprolactam. The standard in free basicity varies depending on every user and is not restricted. It is required that the product usually have free basicity of about 1 meq/kg or less, preferably about 0.3 meq/kg or less, more preferably about 0.1 meq/kg or less. It is known that when free basicity in the product, ε-caprolactam, is high, reverse influence is exerted in polymerization to a nylon.

SUMMARY OF THE INVENTION

Under such circumstances, the present inventors have intensively studied to find an industrially advantageous method for producing ε-caprolactam having low free basicity and providing high yield. As a result, the present inventors have found that when ε-caprolactam is obtained by gas phase Beckman rearrangement reaction using a solid catalyst in the presence of alcohol with using cyclohexanone oxime as a raw material, AAH is usually produced and present in the reaction product in a selectivity of from about 0.1% to about 10% depending on the reaction conditions, and that when the AAH is contained in ε-caprolactam, the presence of the AAH causes to enhance free basicity and reduce qualities of the product, and that when the reaction product is treated with water, the free basicity is reduced and yield of ε-caprolactam is increased due to conversion of the AAH with water into ε-caprolactam, completing the present invention.

First, the present invention provides a method for producing ε-caprolactam which comprises the step of treating, with water, a reaction product containing 1-aza-2-alkoxy-1-cycloheptene, which is obtained by gas phase Beckmann rearrangement reaction of cyclohexanone oxime using a solid catalyst in the presence of alcohol, to eliminate the 1-aza-2-alkoxy-1-cycloheptene.

Secondly, the present invention provides a method for producing ε-caprolactam which comprises the steps of separating a component comprising 1-aza-2-alkoxy-1-cycloheptene from a reaction product containing 1-aza-2-alkoxy-1-cycloheptene obtained by gas phase Beckmann rearrangement reaction of cyclohexanone oxime using a solid catalyst in the presence of alcohol, and treating the separated component comprising 1-aza-2-alkoxy-1-cycloheptene with water to eliminate the 1-aza-2-alkoxy-1-cycloheptene.

Thirdly, the present invention provides a method for producing ε-caprolactam according to the above first-described method, wherein the reaction product to be treated with water is a reaction product obtained by substantially separating an alcohol.

Fourthly, the present invention provides a method for producing ε-caprolactam according to the above secondly-described method, wherein the reaction product to be used for separating the component containing 1-aza-2-alkoxy-1-cycloheptene is a reaction product obtained by substantially separating an alcohol.

Fifthly, the present invention provides a method for producing ε-caprolactam, which comprises the steps of separating a component containing 1-aza-2-alkoxy-1-cycloheptene from a reaction product containing 1-aza-2-alkoxy-1-cycloheptene obtained by gas phase Beckmann rearrangement reaction of cyclohexanone oxime using a solid catalyst in the presence of alcohol, treating the separated component containing 1-aza-2-alkoxy-1-cycloheptene with water to convert the 1-aza-2-alkoxy-1-cycloheptene into ε-caprolactam, and put the resulting product into a step prior to the step of separating the component containing 1-aza-2-alkoxy-1-cycloheptene from the gas phase Beckmann rearrangement reaction product.

Sixthly, the present invention provides a method for producing ε-caprolactam according to the above fifthly-described method, wherein the reaction product to be used for separating the component containing 1-aza-2-alkoxy-1-cycloheptene is a reaction product obtained by substantially separating an alcohol.

Seventhly, the present invention provides a method for producing ε-caprolactam by gas phase Beckmann rearrangement reaction of cyclohexanone oxime using a solid catalyst in the presence of alcohol, which comprises the step of treating 1-aza-2-alkoxy-1-cycloheptene generated as a by-product with water so that a 1-aza-2-alkoxy-1-cycloheptene content in the ε-caprolactam is 100 ppm or less.

DETAILED DESCRIPTION OF THE PRESENT INVENTION

ε-Caprolactam in the present invention usually has an AAH content of about 100 ppm or less, preferably about 25 ppm or less, more preferably about 10 ppm or less, and has low free basicity and has excellent qualities.

The ε-caprolactam in the present invention having such physical properties can be produced by, for example, a method in which a reaction product containing AAH obtained by allowing cyclohexanone oxime to react under gas phase reaction conditions using a solid catalyst in the presence of alcohol is treated with water, or preferably a reaction product containing AAH obtained by substantially separating an alcohol from the above-described reaction product is treated with water, or a method in which a component mainly containing AAH is further separated from the reaction product by distillation or the like and then the component is treated with water. By such a water treatment, AAH is converted into ε-caprolactam so that ε-caprolactam having a small AAH content can be obtained.

In the above-described methods, silicon-oxide-containing catalysts, preferably crystalline metallosilicates may be used as the solid catalyst. In particular, it is more preferred to use crystalline metallosilicates having a Si/Me atomic ratio of 500 or more (wherein Me represents one or more metal elements selected from Al, Ga, Fe, B, Zn, Cr, Be, Co, La, Ge, Ti, Zr, Hf, V, Ni, Sb, Bi, Cu, Nb and the like). Also, it is more preferred to use a crystalline silicate composed of silicon dioxide containing substantially no Me component. The Si/Me atomic ratio can be measured by commonly-used analysis means, for example, an atomic absorption method, a fluorescent X-ray method and the like. These catalysts can be produced by known methods. The crystalline metallosilicate and crystalline silicate are known to include various crystalline types, and those having so-called pentasyl structure are preferred.

In the production of ε-caprolactam, a lower alcohol may usually be used as the alcohol to be allowed to exist in the reaction system. Examples of the lower alcohol include alcohol having 6 or less carbon atoms, and specifically, one or more kinds of alcohol selected from methanol, ethanol, n-propanol, isopropanol, n-butanol, sec-butanol, n-amyl alcohol and n-hexanol. Particularly, it is preferred to use one or more kinds of alcohol selected from methanol, ethanol, n-propanol, isopropanol and n-butanol since remarkable effects are manifested in improvement of selectivity to ε-caprolactam and catalyst life. Among them, methanol and ethanol manifest remarkable effects and, therefore, these are particularly preferred in the industrial point of view.

Further, water can also be used together with alcohol in the above-described production of ε-caprolactam. The amount of water to be used is 0.06 to 2.5 times, preferably 0.18 to 1.9 times in terms of molar ratio based on 1 mol of cyclohexanone oxime. The ratio out of this range tends to cause large decrease of catalyst activity. Use of suitable amount of water exhibits effect for improving catalyst life.

The reaction may usually be effected under a pressure of 3 atm or lower. The reaction can also be effected under reduced pressure lower than atmospheric pressure. The reaction may be conducted as a common gas phase catalytic reaction in fixed bed mode or fluidized bed mode. Cyclohexanone oxime as the raw material reacts in a catalyst layer in gaseous phase, and alcohol may be previously mixed with the cyclohexanone oxime or also be supplied to a reaction vessel separately from cyclohexanone oxime. In the case of the fixed bed reaction, it is preferred that cyclohexanone and alcohol are sufficiently mixed and pass through the catalyst layer in such a mixed condition. In the case of the fluidized bed reaction, it is not necessarily required that cyclohexanone oxime and alcohol are previously mixed. They can be supplied separately, and alcohol can also be divided and then added. Alternatively, in the case of the fluidized bed reaction, alcohol may also be added at an upper flow side than cyclohexanone oxime.

Water may also previously be mixed with cyclohexanone oxide and supplied to a reaction vessel, or may also be supplied separately from cyclohexanone oxime. In the case of the fluidized bed reaction, it can be divided and then added.

The amount of alcohol to be allowed to exist in the reaction system may be suitably from 0.1 to 20 times, preferably 10 times or less, and most preferably from 0.3 to 8 times in terms of ratio by weight based on cyclohexanone oxime.

In the reaction system, a compound inactive in the reaction such as benzene, cyclohexane and toluene, or an inert gas such as nitrogen may also be allowed to exist as a dilution gas.

The reaction temperature may usually be from about 250° C. to about 500° C., preferably from about 300° C. to about 450° C., more preferably from about 300° C. to about 400° C. The space velocity (WHSV) of cyclohexanone oxime as the raw material is from about 0.1 to about 40 hr$^{-1}$ (namely, the rate of supplying cyclohexanone oxime per 1 kg of a catalyst is from about 0.1 to about 40 kg/hr). It is selected in the range preferably of from about 0.2 to about 20 hr$^{-1}$, more preferably from about 0.5 to about 10 hr$^{-1}$.

One of the embodiments of the present invention is that a reaction product containing AAH is treated with water under specific conditions wherein the reaction product is obtained by gas phase Beckmann rearrangement reaction of cyclohexanone oxime conducted in the presence of alcohol, and that AAH contained in a reaction product obtained by substantially separating an alcohol beforehand by distillation or the like from the above-described reaction product is treated with water under specific conditions.

Another embodiment of the present invention is that an AAH-condensed fraction and ε-caprolactam having an AAH content of, usually, 100 ppm or less, preferably about 25 ppm or less, more preferably about 10 ppm or less are separated from each other by distillation from a reaction product itself obtained by gas phase Beckmann rearrangement reaction or from a reaction product obtained by separating an alcohol from the above-described reaction product, and then the AAH-condensed fraction is treated with water under specific conditions. The AAH-condensed fraction may contain ε-caprolactam, a by-product having a low boiling point and water. In such a case that the AAH-condensed fraction is previously separated by distillation and then is treated with water, it is preferred that a treated liquid obtained after the water treatment is used and recycled in a step prior to a step of distillation for condensing AAH since a small amount of by-products other than ε-caprolactam as well as ε-caprolactam itself may be contained in the reaction product obtained after the water treatment. This method is especially recommended since there is no need to add a new facility and the existing facilities can be utilized to effectively eliminate by-products made in the water treatment of AAH and effectively recover ε-caprolactam produced by conversion of AAH.

In the above-described gas phase Beckmann rearrangement reaction, AAH is produced in a selectivity usually of from about 0.1% to about 10% as a by-product in the reaction, and is contained in the reaction product. The kind of AAH is different depending on the kind of alcohol utilized in the rearrangement reaction. For example, when methanol is utilized as the alcohol, 1-aza-2-methoxy-1-cycloheptene is produced, when ethanol is utilized, 1-aza-2-ethoxy-1-cycloheptene is produced, and when n-propanol is utilized, 1-aza-2-n-propoxy-1-cycloheptene is produced. The reaction product of gas phase Beckmann rearrangement reaction containing 1-aza-2-alkoxy-1-cycloheptene as a by-product or the component containing 1-aza-2-alkoxy-1-cycloheptene separated from the reaction product is treated with water and the AAH is hydrolyzed and converted into ε-caprolactam to consume the AAH. When AAH exists in ε-caprolactam in a specific concentration or more, free basicity as one of product standards of ε-caprolactam deteriorates.

In the present invention, when the reaction product containing AAH and ε-caprolactam obtained by the above-described reaction is treated with water, the AAH is eliminated and the yield of ε-caprolactam increases, since ε-caprolactam is produced from the AAH. It is preferred that a treated liquid obtained after the water treatment is used and recycled in a step prior to a step of separating alcohol since, due to the water treatment, AAH mainly produce ε-caprolactam and a corresponding alcohol.

The amount of water used in the water treatment may be from about 1 equivalent to about 50 equivalent, preferably from about 3 equivalent to about 30 equivalent to the amount of AAH existing in the reaction system. When the amount of water is less than 1 equivalent, decomposition of AAH is not sufficient. When the water is too much, the water needs to be removed by evaporation or the like from the treated liquid obtained after the treatment, which results in high cost.

The temperature for the treatment depends on the amount of water to be used and may be from about 45° C. to about 250° C., preferably from about 60° C. to about 200° C. Under a condition such that the treatment temperature is higher than the boiling point of water, it is preferred that the treatment is conducted under pressure. The period of time for the treatment is a period enough to hydrolyze the AAH. The higher the temperature is, the shorter the period of tome is needed. The treatment may usually be conducted for about 0.1 hour to about 10 hours, and preferably about 0.5 hour to about 5 hours.

The water to be used in the water treatment may be added from outside of the reaction system. When water exists in an amount needed for the water treatment in the reaction product to be treated with water or in the AAH obtained after distillation from the reaction product, the water can be utilized for the treatment without adding additional water from outside of the reaction system.

In the water treatment of the reaction product containing AAH obtained by the above-described gas phase Beckmann rearrangement reaction method (hydrolysis treatment of AAH), (A) a reaction product containing AAH or (B) an alcohol-removed component obtained after separating alcohol from the reaction product containing AAH is used (hereinafter, (A) together with (B) is sometimes referred to as an AAH-containing component). Examples of the method for the water treatment include (1) a method in which water is added to the AAH-containing component, heat treatment is conducted and then the product is subjected to purification, (2) a method in which only AAH is, or a fraction containing a condensed AAH is separated from the AAH-containing component by fractionation and the like, and then the obtained AAH or the fraction containing the condensed AAH is treated with water to recover it as ε-caprolactam.

Alternatively, examples of the method for water treatment include (3) a method in which when alcohol having lower boiling point than that of water is used in the gas phase Beckmann rearrangement reaction, water is previously added to the rearrangement reaction system, and then the rearrangement reaction product containing the water is treated as it is so as to treat AAH therein, or then AAH is treated with water remaining after allowing alcohol to flow out of the rearrangement reaction product by distillation and other by-products is removed from the resulting product by distillation or the like to obtain a product, ε-caprolactam, and (4) a method in which a reaction product obtained by gas phase Beckman rearrangement reaction is, or a reaction product obtained after removing the alcohol out of the reaction product is contacted with water by extraction using an organic solvent and water as extracting agents, or by crystallization using a solvent containing water, and the like, and removal of other by-products and hydrolysis of AAH are conducted simultaneously, and the like.

Further, examples of the method for water treatment include (5) a method in which a reaction product containing AAH of gas phase Beckmann rearrangement reaction is, or a remaining liquid obtained after previously recovering alcohol is dissolved in an organic solvent which is immiscible with water, and then the resulting solution is allowed to contact with water, to conduct hydrolysis of AAH and extraction of ε-caprolactam simultaneously so that ε-caprolactam containing no AAH is recovered, and the like.

It is also possible to combine these methods with known purification methods using water such as a method for effecting crystallization using water and a method for effecting purification treatment using an aqueous potassium permanganate solution.

In these hydrolysis methods, it is preferred in the viewpoint of easiness in recovering ε-caprolactam to use water in a minimum amount enough to hydrolyze AAH since a large amount of energy is required in a process for separating ε-caprolactam from water.

Therefore, a industrially preferable method is as follow:
from a reaction product containing AAH as a impurity obtained by a gas phase Beckmann rearrangement reaction of cyclohexanone oxime using a solid catalyst in the presence of alcohol, the alcohol is substantially separated with distillation or the like beforehand, and the resulting fraction containing AAH is separated and water is added to the fraction containing AAH so as to convert the AAH into ε-caprolactam.

It is noted that the previous removal of alcohol is preferred since the hydrolysis of AAH may be suppressed in the presence of much alcohol when AAH is treated with water, while the explanation of "an alcohol is substantially separated (or removed) with distillation or the like from the reaction product" is used in the present invention. The amount of alcohol which should be removed is not restricted and varies depending on an amount of water existing in hydrolysis, treatment temperature or the like. Alcohol may preferably be removed in an amount of about 90% or more based on the amount of water existing before the removal.

As described above, the ε-caprolactam of the present invention has low free basicity and preferable qualities, since it usually has 1-aza-2-alkoxy-1-cycloheptene content of 100 ppm or less, preferably 25 ppm or less, more preferably 10 ppm or less. AAH is converted into ε-caprolactam after water treatment and makes the yield of the aimed product high and, therefore, industrial available value thereof is extremely high. In addition, the present invention provides a method for producing ε-caprolactam having a low free basicity with a high yield of the aimed product without additional installation of new facilities for separating or recovering by-products produced by the water treatment, when AAH is separated with distillation or the like from the reaction product to obtain a crude caprolactam having a AAH content of 100 ppm or less, the separated AAH is subjected to the hydrolysis treatment and then the hydrolysis-treated product is recycled and treated in a step prior to the step of separating AAH. Therefore, the present invention has extremely high industrial available values.

EXAMPLE

The present invention is described in more detail by following Examples, which are embodiments thereof and should not be construed as a limitation upon the scope of the present invention.

In the present invention, conversion of cyclohexanone oxime, selectivity to ε-caprolactam and selectivity to AAH were respectively calculated using the following formulae:

Conversion of cyclohexanone oxime $(\%)=[(X-Y)/X]\times 100$

Selectivity to ε-caprolactam $(\%)=[Z/(X-Y)]\times 100$

Selectivity to AAH $(\%)=[W/(X-Y)]\times 100$ wherein X, Y and Z respectively represent the followings:
X=molar amount of cyclohexanone oxime supplied
Y=molar amount of cyclohexanone oxime unreacted
Z=molar amount of ε-caprolactam in a product
W=molar amount of AAH in a product

Reference Example 1

0.375 g of a crystalline zeolite-containing catalyst was packed in a quartz reaction tube having an internal diameter of 6 mm φ and a length of about 60 cm heated to 370° C. (catalyst layer height: about 23 mm). Raw material liquid having a ratio by weight of cyclohexanone oxime/methanol/water of 1/1.89/0.052 was introduced into reaction tube at a rate of 8.54 g/h under nitrogen gas flow of 140 cc/min as a carrier gas. The temperature of catalyst layer ( i.e. reaction temperature) was 380° C. The resulting reaction product was cooled and collected from the outlet of the reaction tube in a dry ice/methanol bath. The reaction product was analyzed by gas chromatograph. As a result, the conversion of cyclohexanone oxime was 99.4%, the selectivity to ε-caprolactam was 96.6%, and the selectivity to 1-aza-2-methoxy-1-cycloheptene (hereinafter, abbreviated as AMH) was 0.82%.

Reference Examples 2 to 4

0.375 g of a crystalline zeolite-containing catalyst was packed in a quartz reaction tube having an internal diameter of 10 mm φ and a length of about 60 cm heated to 325° C. (catalyst layer height: about 23 mm). Raw material having a ratio by weight of cyclohexanone oxime/alcohol/water of 1/1.89/0.052 was introduced at a rate of 8.54 g/h under nitrogen gas flow of 70 cc/min, and the reaction gas was collected from the outlet of the reaction tube in a dry ice/methanol bath. The temperature of the catalyst layer was from 360° C. to 370° C. The reaction liquid was analyzed by gas chromatograph. The results are shown in Table 1.

Reference Example 5

The procedure was conducted in the same manner as in Reference Examples 2 to 4 except that the raw material having a ratio by weight of cyclohexanone oxime/utilized alcohol/water of 1/5.26/0.052 was introduced at a rate of 18.0 g/h to obtain a reaction liquid and the reaction liquid was analyzed by gas chromatograph. The results are shown in Table 1.

TABLE 1

| Reference Example | 2 | 3 | 4 | 5 |
|---|---|---|---|---|
| Name of alcohol | Methanol | Ethanol | n-Propanol | n-Propanol |
| A (molar ratio) | 6.4 | 4.4 | 3.4 | 9.3 |
| B (%) | 99.73 | 99.23 | 97.69 | 87.49 |
| C (%) | 95.37 | 95.78 | 94.92 | 94.36 |
| D (%) | 0.79 | 0.32 | 0.04 | 0.29 |

Note:
A: molar ratio of alcohol/cyclohexanone oxime
B: conversion of cyclohexanone oxime
C: selectivity to ε-caprolactam
D: selectivity to AAH

Example 1

Into 319 g of reaction liquid obtained by gas phase Beckmann rearrangement reaction (having 15.8% by weight of lactam and 0.19% by weight of AMH, by gas chromatograph analysis) were added 8.50 g of AMH and 6.77 g of water. This reaction liquid was refluxed in a fractionation tower packed with about 5-stage glass helipack filler at a reflux ratio of 1 with raising the bath temperature from 80 C to 130° C. over 3 hours, to distill off methanol. The bath was controlled at 140° C. at normal pressure, heated for 3 hours, and then, cooled to obtain 88.9 g of a remaining liquid. Gas chromatograph analysis was conducted to find that lactam content was 63.6% and AMH was not detected. The production ratio of lactam based on AMH was 74.2%.

It is noted that production ratio of lactam based on AMH and remaining ratio of AMH were respectively calculated using the following formulae:

Production ratio of lactam based on AMH$(\%)=[(B-A)/C]\times 100$

Remaining ratio of AMH $(\%)=(D/C)\times 100$

A=molar amount of ε-caprolactam in a raw material used for water treatment
B=molar amount of ε-caprolactam in a product obtained after water treatment
C=molar amount of AMH in a raw material used for water treatment
D=molar amount of AMH in a product obtained after water treatment

Reference Examples 6 to 9

Hydrolysis of AMH was carried out by treating AMH contained in a lactam compound with water using one kind of lactam, 2-pyrrolidone rather than using ε-caprolactam, in order to accurately investigate a production yield of ε-caprolactam, which is a product obtained by hydrolysis of AMH.

2-Pyrrolidone, AMH, water and methanol were used in a ratio by weight of 2-pyrrolidone/AMH/water/methanol of 20.0/1.0/1.0/36.6, and heated at temperature for hours shown in Table 2. The reaction product was analyzed by gas chromatograph to measure production ratio of lactam and remaining ratio of AMH in the reaction product. The results are shown in Table 2.

Reference Example 10

The procedure was conducted in the same manner as in Reference Examples 6 to 8 except that 2-pyrrolidone, AMH and water were used in a ratio by weight of 2-pyrrolidone/ AMH/water of 20.0/1.0/1.0, to analyze the reaction product and measure production ratio of ε-caprolactam and remaining ratio of AMH in the reaction product. The results are shown in Table 2.

TABLE 2

| No. of Reference Example | 6 | 7 | 8 | 9 | 10 |
|---|---|---|---|---|---|
| Heating temperature × time (hour) | 65° C. × 1 | 65° C. × 6 | 45° C. × 3 | 140° C. × 1 | 140° C. × 3 |
| Production ratio of lactam (%) | 4.4 | 21.1 | 3.4 | 65.3 | 78.9 |
| Remaining ratio of AMH (%) | 90.7 | 62.6 | 89.7 | 3.6 | 0 |

Example 2

The free basicity of ε-caprolactam containing AMH in an amount shown in Table 3 was measured. The results thereof are shown in Table 3.

Measuring method:

(1) Into a beaker charged with 10.0 g of water, was added a methyl red-methylene blue indicator, and the color of the solution was adjusted to grayish blue color (pH 5.70) using an aqueous dilute sodium hydroxide solution or N/100 normal solution of sulfuric acid while stirring.

(2) 10.00 g of sample, ε-caprolactam, was added and dissolved.

(3) Using the N/100 normal solution of sulfuric acid, was titrated the resulting solution with an automatic buret to obtain an amount of sulfuric acid used for reaching pH of 5.70 or changing the color of the indicator to grayish blue, which was shown in terms of base equivalent amount per 1 kg of lactam (meq/kg).

TABLE 3

| AMH content (ppm per lactam) | Free basicity (meq/kg) |
|---|---|
| 0 | 0.033 |
| 1.3 | 0.043 |
| 2.5 | 0.054 |
| 7.5 | 0.093 |
| 25 | 0.210 |
| 100 | 0.723 |

Example 3

0.375 g of a crystalline zeolite-containing catalyst was packed in a quartz reaction tube having an internal diameter of 6 mm φ and a length of about 60 cm heated to 370° C. (catalyst layer height: about 23 mm). Raw material having a ratio by weight of cyclohexanone oxime/methanol/water of 1/1.89/0 was introduced into the reaction tube at a rate of 8.54 g/h under nitrogen gas flow of 140 cc/min as a carrier gas. The temperature of catalyst layer (i.e. reaction temperature) was from 365 to 370° C. The resulting reaction product was cooled and collected from the outlet of the reaction tube in a dry ice/methanol bath. The reaction product was analyzed by gas chromatograph. As a result, the conversion of cyclohexanone oxime was 97.3%, the selectivity to ε-caprolactam was 95.2%, and the selectivity to AMH was 1.77%.

100 g of the reaction product was condensed with an evaporator under reduced pressure to obtain 35.1 g of crude lactam. This lactam was analyzed with gas chromatograph to find that ε-caprolactam was 92.57%, cyclohexanone oxime was 2.74% and AMH was 1.64% in terms of a percentage area calculated excluding an area of solvent peak.

Into 30 g of the crude lactam, was added 1.0 g of water. Then the resulting lactam solution was heated at 140° C. for 2 hours in an autoclave. This solution was analyzed with gas chromatograph to find that ε-caprolactam was 93.82% and oxime was 2.75% in terms of a percentage area calculated excluding an area of solvent peak. AMH was not detected.

What is claimed is:

1. A method for producing ε-caprolactam which comprises the step of treating, at a temperature of from 45° C. to 200° C. with water, a reaction product containing 1-aza-2-alkoxy-1-cycloheptene, which reaction product is obtained by gas phase Beckmann rearrangement reaction of cyclohexanone oxime using a solid catalyst in the presence of alcohol, to obtain an ε-caprolactam product having 100 ppm or less of the 1-aza-2-alkoxy-1-cycloheptene.

2. A method for producing ε-caprolactam which comprises the steps of separating a component comprising 1-aza-2-alkoxy-1-cycloheptene from a reaction product containing 1-aza-2-alkoxy-1-cycloheptene obtained by gas phase Beckmann rearrangement reaction of cyclohexanone oxime using a solid catalyst in the presence of alcohol, and treating the separated component comprising 1-aza-2-alkoxy-1-cycloheptene with water at a temperature of from 45° C. to 200° C. to eliminate the 1-aza-2-alkoxy-1-cycloheptene from said separated component.

3. A method for producing ε-caprolactam according to claim 1, wherein the reaction product to be treated with water is a reaction product obtained by substantially separating an alcohol.

4. A method for producing ε-caprolactam according to claim 2, wherein the reaction product to be used for separating the component containing 1-aza-2-alkoxy-1-cycloheptene is a reaction product obtained by substantially separating an alcohol.

5. A method for producing ε-caprolactam according to any one of claims 1–4, wherein the water treatment is conducted under a heating condition for a period of time of from 0.5 to 2 hours.

6. A method for producing ε-caprolactam according to claim 2 or 4, wherein the step of separating the component containing 1-aza-2-alkoxy-1-cycloheptene from the reaction product is conducted by distillation treatment.

7. A method for producing ε-caprolactam, which comprises the steps of separating a component containing 1-aza- 2-alkoxy-1-cycloheptene from a reaction product containing 1-aza-2-alkoxy-1-cycloheptene obtained by gas phase Beckmann rearrangement reaction of cyclohexanone oxime using a solid catalyst in the presence of alcohol, treating the separated component containing 1-aza-2-alkoxy-1-cycloheptane with water at a temperature of from 45° C. to 200° C. to convert the 1-aza-2-alkoxy-1-cycloheptene into an ε-caprolactam product, and combining the resulting product with said gas phase Beckmann rearrangement reaction product prior to said separation step.

8. A method lot producing ε-caprolactam according to claim 7, wherein said component is separated from said reaction product obtained by gas phase Beckmann rearrangement from which alcohol has been substantially removed.

9. A method according to any one of claims 1–4, 7 or 8 for producing ε-caprolactam obtained by gas phase Beckman rearrangement reaction of cyclohexanone oxime using a solid catalyst in the presence of alcohol, which comprises the step of treating by-product 1-aza-2-alkoxy-1-cycloheptene with water so that a 1-aza-2-alkoxy-1-cycloheptene content in the resulting ε-caprolactam is 25 ppm or less.

10. A method according to any one of claims 1–4, 7 or 8 for producing ε-caprolactam obtained by gas phase Beckmann rearrangement reaction of cyclohexanone oxime using a solid catalyst in the presence of alcohol, which comprises the step of treating by-product 1-aza-2-alkoxy-1-cycloheptene with water so that a 1-aza-2-alkoxy-1-cycloheptene content in the resulting ε-caprolactam is 10 ppm or less.

11. A method for producing ε-caprolactam according to any one of claims 1–4, 7 or 8, wherein the amount of water to be used for the treatment is from about 3 equivalent to about 30 equivalent to the amount of 1-aza-2-alkoxy-1-cycloheptene.

12. A method for producing ε-caprolactam according to any one of claims 1–4, 7, or 8, wherein the amount of water to be used for the treatment is from about 3 equivalent to 14.4 equivalent to the amount of 1-aza-2-alkoxy-1-cycloheptene.

* * * * *